US00PP13968P39

(12) United States Plant Patent
Hirabayashi

(10) Patent No.: US PP13,968 P3
(45) Date of Patent: Jul. 15, 2003

(54) PETUNIA PLANT NAMED 'KEIYEUL'

(75) Inventor: Hiroshi Hirabayashi, deceased, late of Yachiyo (JP), by Eriko Hirabayashi, Minako Hirabayashi, Kanako Hirabayashi, legal representatives

(73) Assignee: Keisei Rose Nuseries, Inc., Tokyo (JP)

( * ) Notice: Subject to any disclaimer, the term of this patent is extended or adjusted under 35 U.S.C. 154(b) by 0 days.

(21) Appl. No.: 09/929,136

(22) Filed: Aug. 13, 2001

(65) Prior Publication Data

US 2003/0033653 P1 Feb. 13, 2003

(51) Int. Cl.[7] ..... A01H 5/00

(52) U.S. Cl. ..... Plt./356

(58) Field of Search ..... Plt./356

(56) References Cited

PUBLICATIONS

UPOV–ROM GTITM Computer Database, 2001/06, GTI Jouve Retrieval Software, citation for 'Keiyeul'.*

* cited by examiner

*Primary Examiner*—Bruce R. Campell
*Assistant Examiner*—Susan B. McCormick
(74) *Attorney, Agent, or Firm*—Klarquist Sparkman, LLP

(57) ABSTRACT

Petunia plant having a vigorous habit and profuse flowering of very light yellow colored flowers.

2 Drawing Sheets

GENUS AND SPECIES

*Petunia hybrida.*

VARIETY DENOMINATION

KEIYEUL.

BACKGROUND OF THE INVENTION

The primary objective of this breeding was to produce a new petunia variety having large, single, yellowish color flowers; a free flowering, pendant habit; and free branching.

BRIEF SUMMARY OF THE INVENTION

The objective was substantially achieved, along with other desirable improvements, as evidenced by the following unique combination of characteristics that are outstanding in the new variety an that distinguish it from its parents, as well as from all other varieties:

1. Vigorous habit; and
2. Profuse flowering.

DETAILED DESCRIPTION OF THE INVENTION

Asexual reproduction of this new variety by cuttings, as performed at Keisei Rose Nurseries, Inc., Yachiyo-shi, Chiba-ken, Japan and at Somis, Calif. shows that the foregoing and all other characteristics and distinctions come true to form and are established and transmitted through succeeding propagations.

COMPARISON WITH A SIMILAR VARIETY

As compared with 'CALIFORNIA GIRL', the flower color is paler but 'KEIyeul's' habit is stronger and growth habit is more vigorous.

BRIEF DESCRIPTION OF THE ILLUSTRATION

The accompanying illustrations show a typical specimen of this new variety, depicted in color as nearly true as it is reasonably possible to make the same in a color illustration of this character:

DETAILED BOTANICAL DESCRIPTION

Figure 1:
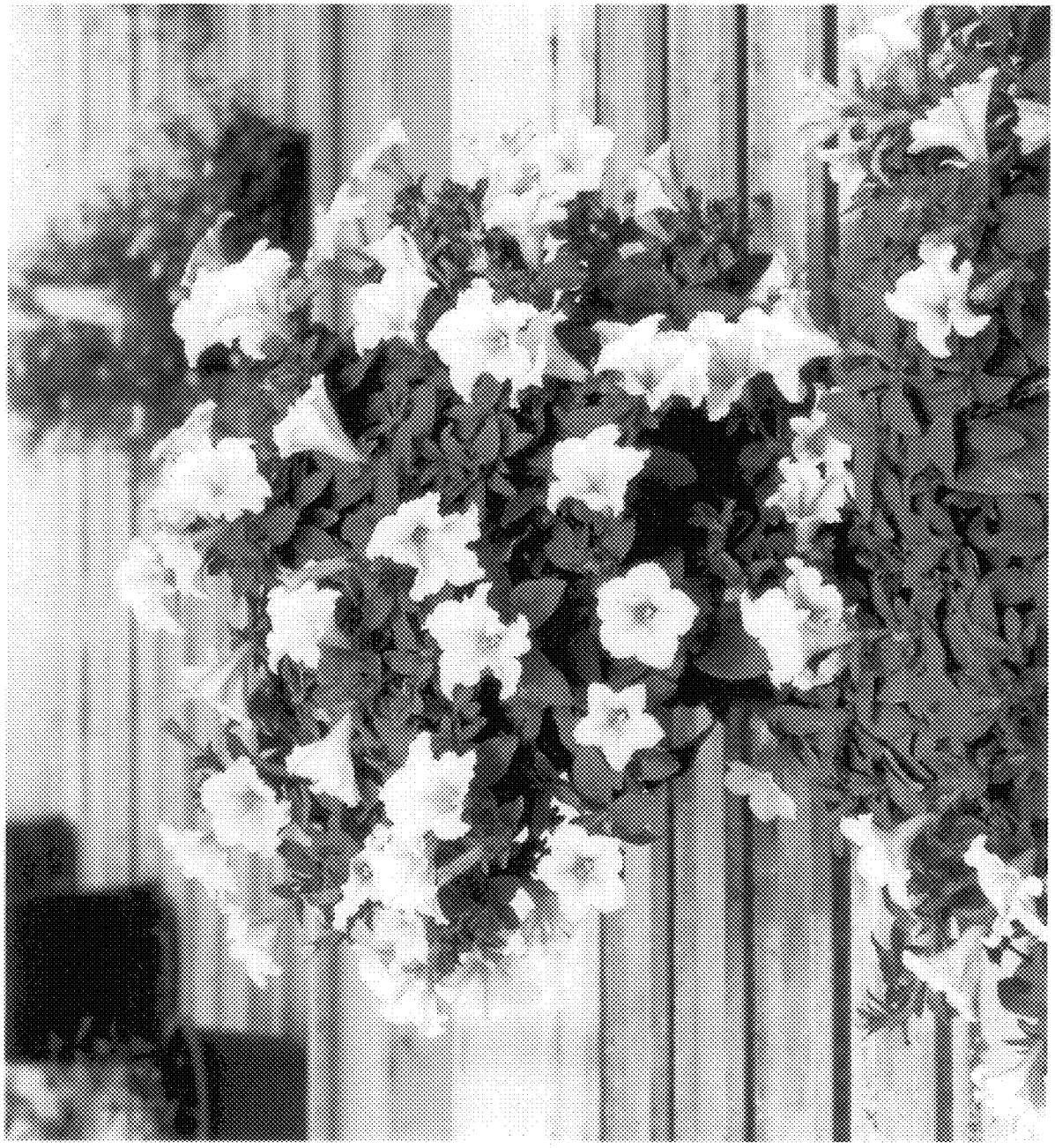
FIG. 1 is a photograph of a mature plant.
Figure 2:
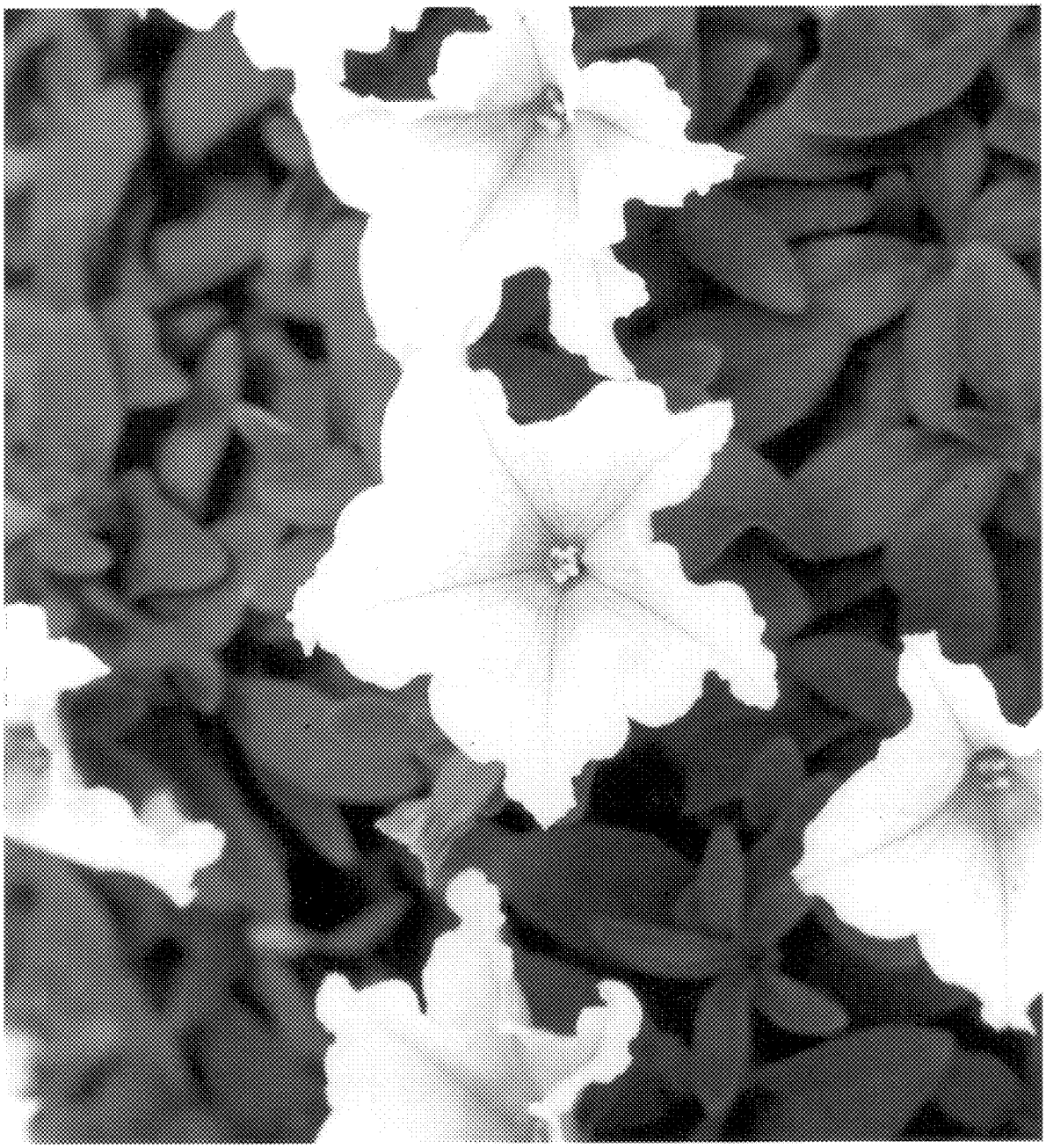
FIG. 2 is an enlarged view of a single flower and portions of adjacent flowers.

The following is a detailed description of my new petunia cultivar with color descriptions using terminology in accordance with The Royal Horticultural Society (London) Colour Chart, except where ordinary dictionary significance of color is indicated.

Parentage:

*Seed parent.*—Unnamed seedling (unpatented).

*Pollen parent.*—Unnamed seedling (unpatented).

Flower: Observations made form specimens beginning at three months of age, grown in a garden environment at Somis, Calif. in July, 2000 to December, 2000.

*Growth.*—Spreading.

*Growth habit.*—Vigorous, spreading.

*Mature plant.*—Height: 11–15 cm. Spreading area: 50–75 cm in diameter.

*Blooming period.*—From time day length exceeds twelve hours to first frost.

*Stem.*—Overall Length: 11–20 cm. Main Stem: 20 cm. Laterals: 11–15 cm. Thickness: 2–3 mm. Color: Yellow Group 9D. Pubescence: Pubescent. Mode of Branching: Abundant Length of Internode: 2.20–2.50 cm (short).

*Leaf.*—Arrangement on stem: Slantly upward. Shape: Elliptic. Size: Width: 3.5 Length: 5.0 cm. Thickness: About 1 mm. Base Shape: Acute. Apex Shape: Acute. Surface texture: Smooth. Color: Upper Surface: Yellow-Green Group 144A. Lower Surface:

Yellow-Green Group 144A. Phyllotaxis: Perpendicular. Pubescence: Pubescent. Venation Pattern: Pinnate. Vein Color: Yellow-Green Group 144A. Margins: Smooth. Petiole: None present.

Flower:

*Orientation at opening.*—Slantly upward.

*Size.*—2–2⅜ inches in diameter.

*Type.*—Single.

*Shape.*—Corolla is long (5.2 cm) and tubular (5.9 cm wide.)

*Color.*—The upper sides of the petals are Yellow Group 11D with five prominent veins of Yellow-Green Group 155A. The base of the throat of a flower is Yellow-Green Group 145C. The reverse sides of the petals are White Group 155D with five prominent veins of Yellow-Green Group 145C. The base of the throat is Yellow-Green Group 145C.

*Peduncle.*—Length: 1.3–1.8 cm. Diameter: 0.5 cm. Color: Yellow-Green Group 146C.

*Calyx.*—Number of sepals: 5. Length: 15–17 mm. Color: Yellow-Green Group 144A.

*Petals.*—Shape: Obverse. Margin: Smooth. Apex: Acute. Texture: Smooth.

Reproductive parts:

*Stamens.*—Number: Five.

*Anthers.*—Color: Yellow-White Group 158B.

*Filaments.*—Color: White Group 155A.

*Pistil.*—Quantity: One.

*Stigma.*—Color: Green Group 143A.

*Style.*—Color: Yellow-Green Group 149C.

*Fruit.*—None observed.

Disease resistance: Resistant to mildew under normal growing conditions.

Response to climatic conditions: Hardy to Zone 10.

I claim:

1. A new and distinct variety of petunia plant, substantially as herein shown and described, characterized particularly by its vigorous habit and profuse very light yellow colored flowers.

* * * * *